United States Patent

Zilch et al.

[11] Patent Number: 5,955,452
[45] Date of Patent: Sep. 21, 1999

[54] COVALENT LIPID-PHOSPHONO-CARBOXYLIC ACID CONJUGATES AND APPLICATION THEREOF AS ANTIVIRAL MEDICAMENTS

[75] Inventors: Harald Zilch, Mannheim; Dieter Herrmann, Heidelberg; Hans-George Opitz, Weinheim; Gerd Zimmermann, Mannheim; Edgar Voss, Viernheim, all of Germany

[73] Assignee: Roche Diagnostics GmbH, Mannheim, Germany

[21] Appl. No.: 09/077,894

[22] PCT Filed: Dec. 16, 1996

[86] PCT No.: PCT/EP96/05648

§ 371 Date: Aug. 26, 1998

§ 102(e) Date: Aug. 26, 1998

[87] PCT Pub. No.: WO97/22368

PCT Pub. Date: Jun. 26, 1997

[30] Foreign Application Priority Data

Dec. 15, 1995 [DE] Germany .................. 19547022

[51] Int. Cl.⁶ .................................................... A01N 57/00
[52] U.S. Cl. ................... 514/79; 514/89; 514/91; 514/114; 514/119; 514/121; 514/126; 514/129; 514/143; 514/885; 540/542; 546/22; 548/112; 554/40; 554/41; 554/42; 554/44; 554/46; 554/61; 554/63; 554/79; 554/80; 554/84; 562/11; 562/15; 564/152; 564/155; 564/161; 564/162; 564/168; 564/169; 568/11; 568/17

[58] Field of Search ......................... 564/152, 155, 564/161, 162, 168, 169; 568/11, 17; 562/11, 15; 548/112; 546/22; 540/542; 554/40, 41, 42, 44, 46, 61, 63, 79, 80, 81; 514/79, 89, 91, 114, 119, 121, 126, 129, 143, 885

*Primary Examiner*—Deborah D. Carr
*Attorney, Agent, or Firm*—Nikaido, Marlmelstein, Murray & Oram LLP

[57] ABSTRACT

The present invention concerns new lipid derivatives of phosphonocarboxylic acids of the general formula I,

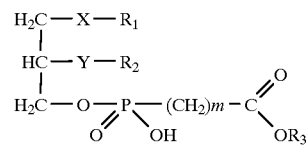

in which the meaning of the symbols is elucidated in the description, tautomers thereof and their physiologically tolerated salts of inorganic and organic bases as well as processes for the production thereof and pharmaceutical agents containing these compounds.

16 Claims, No Drawings

COVALENT LIPID-PHOSPHONO-CARBOXYLIC ACID CONJUGATES AND APPLICATION THEREOF AS ANTIVIRAL MEDICAMENTS

This application is a 371 of PCT/EP96/05648 filed Dec. 16, 1996.

The present invention concerns new lipid derivatives of phosphonocarboxylic acids and their esters of the general formula I,

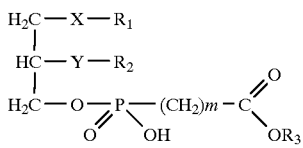

in which

R$^1$ is a straight-chained or branched, saturated or unsaturated alkyl chain in a group —(CH$_2$)$_e$-Cycl in which e corresponds to an integer between 4 and 16, and one of the carbon atoms from position 3 onwards can be replaced by a heteroatom (oxygen, nitrogen or sulfur), R$^2$ can be hydrogen, a straight-chained or branched, saturated or unsaturated alkyl chain with 1–20 carbon atoms R$^3$ represents a straight-chained or branched alkyl chain with 1–6 carbon atoms, preferrably methyl, ethyl, propyl, isopropyl, butyl, isobutyl, t-butyl, pentyl, hexyl, neopentyl, thexyl or phenyl, choline, ethanolamine, carnitine, C$_5$–C$_7$-cycloalkyl residue, benzyl or one of the following groups

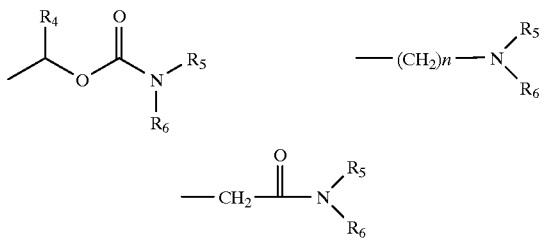

wherein R$_4$ represents C$_1$–C$_6$-alkyl, benzyl or phenyl and R$_5$ and R$_6$ C$_1$–C$_6$-alkyl and n 1,2 or 3, X denotes a valency dash, oxygen, sulfur, oxycarbonyl, carbonyloxy, carbonylamido, amidocarbonyl, a sulfinyl or a sulfonyl group, Y denotes a valency dash, oxygen, sulfur, oxycarbonyl, carbonyloxy, carbonylamido, amidocarbonyl, a sulfinyl or a sulfonyl group, Cycl represents an alkyl residue with 5–7 C atoms or phenyl in which one ring carbon atom can be replaced by nitrogen and the saturated or aromatic rings can be substituted once or several times by C$_1$–C$_{10}$ alkyl, C$_1$–C$_{10}$ alkoxy, C$_1$–C$_{10}$ alkyl-mercapto or halogen, m represents 0, 1, 2 or 3, provided that R$^1$ can be the same as R$^2$ if R$^2$ at the same time has the meaning of R$^1$, which means R$^1$ and R$^2$ can be exchanged in their meanings tautomers thereof, their physiologically tolerated salts of inorganic or organic bases as well as processes for the production thereof and pharmaceutical agents containing these compounds.

Since the compounds of the general formula I contain asymmetric carbon atoms all optically active forms and racemic mixtures of these compounds are also a subject matter of the present invention.

The therapy of malignant neoplasias (carcinomas, sarcomas, haematological neoplasias), inflammatory diseases or autoimmune diseases as well as diseases caused by viruses or retroviruses such as for example AIDS, ARC (ADS related complex), cytomegaly, herpes infections or hepatitis, is often also accompanied by their extreme side effects in addition to the inadequate efficacy of the therapeutic substances used. This effect can be explained by the inadequate in vivo selectivity and limited therapeutic range of the pharmacologically active substances used. The advantageous pharmacological in vitro properties of the pharmacologically active substances can often not be transferred to in vivo conditions.

It has therefore been attempted for years to provide new substances with improved properties with regard to their therapeutic range by modifying the chemical structure of pharmacologically active substances. Moreover new pharmaceutical forms of administration are often developed with the aim of transporting the active substances specifically to their site of action at which they are intended to display their therapeutic action. In this case it is particularly intended to avoid undesired interaction with healthy cells. In the case of tumour cells which have corresponding surface antigens, antibodies have for example been produced that recognize these special surface antigens and thus selectively bind to the cancer cell. The antibodies are modified with suitable toxins in such a way that the toxin is released after binding to the cancer cell is completed and the cancer cell is killed. Another alternative to improve the therapeutic range is to change the physical properties of the underlying active substance in such a way that the solubility or tolerance of the active substance is improved by slight modification of the pharmacologically active substance for example by producing acid or base addition salts or by preparing pharmacological safe esters [for example fatty acid esters; J. Pharm. Sci. 79, 531 (1990]. These slightly chemically modified compounds are often denoted "prodrugs" since they are almost immediately converted into the therapeutically active agent on contact with body fluids or in the liver (first pass metabolism). Said prodrugs are enclosed by this invention.

In order to improve catabolic stability, nucleosides such as e.g. ara-C and ara-A have been chemically bound to phospholipids. The corresponding derivatives exhibited less toxicity and higher stability in vivo compared to unmodified nucleosides. The absorption and cell penetration were, however, hardly influenced. [J. Med. Chem. 32, 367 (1989), Cancer Res. 37, 1640 (1977) and 41, 2707 (1981)]. Further phospholipid derivatives of nucleosides are for example known from the following literature references:

The production and use of liponucleotides as antiviral pharmaceutical agents is described in J. Biol. Chem. 265, 6112 (1990). However, in this case only dimyristoylphosphatidyl and dipamitylphosphatidyl residues coupled to known nucleosides such as AZT and ddC with their fatty acid ester structure were investigated and synthesized.

Nucleoside conjugates of thioether lipids with cytidine diphosphate which have an antitumoral action and could be used in oncology are described in J. Med. Chem. 33 1380 (1 990).

In Chem. Pharm. Bull. 36, 209 (1988) 5'-(3-SN-phosphatidyl)-nucleosides having antileukaemic activity are described as well as their enzymatic synthesis from the appropriate nucleosides and phosphocholines in the presence of phospholipase D with transferase activity.

The enzymatic synthesis of liponucleotides is also described inter alia in Tetrahedron Lett. 28, 199 (1987) and Chem. Pharm. Bull. 36, 5020 (1988).

WO 94/13324 describes orally available active substances with 1-O-alkyl-, 1-O-acyl-, 1-S-acyl- and 1-S-alkyl-sn-glycero-3-phosphates as lipid carriers.

The application EP 418814 and J. Med. Chem. 34, 1912 (1991) describe isoprenoidphosphinylformates as squalene synthetase inhibitors.

In Biochem. Biophys. Res. Cornmun. 171, 458 (1990) a lipid conjugate of the antiretroviral Foscarnet with palmitylphosphonoformate is described and the anti-HIV activity of (hexyloxy)-hydroxyphosphinylacetic acid is demonstrated in J. Med. Chem. 20, 660 (1977).

In general it is very advantageous to find effective ways of transporting concentrations of therapeutic pharmaceutical substances into the respective target organs or target cells, in the case of AIDS into the cells of the immune system and the lymphatic system which are considered to be the main reservoir of viral replication.

PFA (phosphonoformic acid) and PAA (phosphonoacetic acid) have good antiviral activity against HSV 1 and 2, influenza, HBV, VZV, EBV as well as retroviral infections.

PFA/PAA and derivatives thereof may under certain circumstances be an effective alternative/supplement to nucleosides since they inhibit a broad spectrum of DNA and RNA polymerases as well as the RT of retroviruses with adequate selectivity.

PFA and PAA themselves are toxic due to their similarity to pyrophosphate by accumulation in bones.

The compounds of the present invention also have valuable pharmacological properties. They are in particular suitable for the therapy and prophylaxis of infections that are caused by DNA viruses such as the herpex simplex virus, the cytomegaly virus, papova viruses, the varicella zoster virus, the hepatitis viruses or Epstein-Barr virus or RNA viruses such as Toga viruses or especially retroviruses such as the oncoviruses HTLV-I and II as well as the lentiviruses visna and human immunodeficiency virus HIV-1 and 2.

The compounds of formula I appear to be particularly suitable for treating the clinical manifestations of retroviral HIV infection in humans such as persistent generalized lymphadenopathy (PGL), the advanced stage of the ADS-related complex (ARC) and the complete clinical picture of AIDS as wel as the associated CMV and HSV infections.

The antiviral/antiretroviral action of Foscamet (phosphonoformic acid trisodium salt/PFA) in HIV patients with CMV retinitis is described in J. Infect. Dis. 172, 225 (1995).

The antiviral action in murine CMV is described in Antiviral Res. 26, 1 (1995)

In addition PFA is utilized in JAMA 273, 1457 (1995) for the treatment of CMV retinitis.

PFA- and PAA-2',3'-dideoxy-3'-thiacytidine conjugates which inhibit HIV-1 replication are shown in J. Med. Chem. 37, 2216 (1994) and acyloxyalkyl esters of Foscarnet are described in J. Pharm. Sci. 83, 1269 (1994).

The U.S. Application U.S. Pat. No. 5,194,654 and the PCT-Application WO 94/13682 are also of particular interest. Lipid derivatives of phosphonocarboxylic acids and their use in liposomes with formation of a particularly stable liposomal complex are described therein. Apart from an extremely broad and very speculative claim, 1-O-alkyl-sn-glycero-3-phosphonocarboxylic acids are described as the core of the application which are incorporated particularly well into the lipid bilayer of liposomes. The claimed alkyl residues can comprise 2–24 carbon atoms but are not additionally substituted.

Only the compound 1-O-octadecyl-sn-glycero-3-phosphono-formate (batyl-phosphonoformate) is described as an example and supported by data for an antiviral action.

This compound proved to be unstable in investigations that were carried out and during production. In contrast to the said patent applications the compound is used as the pure substance in solution/suspension and not in liposomes.

The compounds of the general formula I according to the invention are stable under the same conditions and have clear advantages in vitro as well as in vivo (model in the mouse).

The lipidphosphonocarboxylic acid esters are in vitro as effective as the respective free carboxylic acids. In vivo, they are clearly advantageous, especially with oral medicamentation action. The carboxylic acid esters of the compounds of formula I show under acid conditions a decreased destruction by decarboxylation and therefore an improved bioavailability. Therefore the therapeutic dose can be reduced compared with the respective free carboxylic acids. Furthermore, the membrane permeability is optimized, e.g. by passing through the blood-brain-barrier or the cell membrane of the cell of interest. Because the carboxylic acid ester has to be cleaved in vivo by esterases, the half life time is prolonged in serum.

The compounds claimed in this application represent an interesting extension compared to WO 94/13682 and U.S. Pat. No. 5,194,654 although they are not encompassed by these applications.

The compounds of formula I are new. In addition to the improved stability (in substance and in solution) the claimed compounds also have a better action compared to the known lipid derivatives.

Surprisingly the pharmaceutically active substances of formula I have a larger therapeutic range compared to the pharmacologically active free or unmodified substances. Moreover they improve their retention time in the body, the bioavailability or the membrane permeability (e.g. blood-brain barrier, cell membrane etc.) of the pharmacologically active substances which is often known to be a critical factor. Compounds of formula I thus serve as a carrier system (carrier) for the pharmacologically active substances. With regard to their function the conjugates of formula I can be referred to as an intracellular drug storage, drug targeting and drug delivery system. They enable the pharmacologically active substance to be released intracellularly after oral administration and advantageously this release does not take place unspecifically in all cells, organs or tissues of the body but specifically in those cells that contain a particular enzyme. However, it is particularly surprising that cleavage does not already occur during the transport of the substrate through the body fluids such as blood, serum or lymph fluid or through the liver but only on or in the respective target cells. In this way undesired excretion of the phosphonocarboxylic acid by the kidney or cleavage of the conjugate in the liver is avoided so that the major part of the active substance is transported to or into the respective target cells. As already stated above such cells are in particular physiologically or pathophysiologically activated cells which come into consideration as a target object for the administration of pharmacologically active substances such as for example blood leucocytes, lymphocytes, macrophages and other cell populations of the immunological lymphatic system. These are in particular activated cells (e.g. macrophages, granulocytes, lymphocytes, leucocytes, thrombocytes, monocytes etc.) which play a pathophysiological or symptomatic role in the respective disease process. In addition these are also cells which are infected by viruses, bacteria, fungi or other microorganisms.

Surprisingly it was also found that the therapeutic range of a pharmacologically active phosphonocarboxylic acid and ist esters are significantly improved when the substance is coupled to a very special lipid-like carrier molecule. The conjugate prepared in this way serves as a new active substance for the production of pharmaceutical forms of administration. On the whole the coupling results in an increased in vivo effect of the pharmaceutically active phosphonocarboxylic acid since the pharmacologically active substance is localized in the target cells by the resulting drug delivery transport system and hence the efficiency and tolerance of the pharmacologically active substance is improved. This means that on the one hand the amount of the pharmacologically active phosphonocarboxylic acid to be administered can be reduced or on the other hand it is possible to achieve an increased pharmacological effect while retaining the same effective amount.

The pharmacologically active phosphonocarboxylic acid is released from the conjugate by enzymatic hydrolysis of the conjugate.

The conjugates of formula I exhibit significant advantages in comparison with the unconjugated pharmacologically active phosphonocarboxylic acid and ist esters. The specific carrier covalently bound to the pharmacologically active substance improves the bioavailability of the poorly resorbed pharmacologically active substances, the tolerance of potentially toxic active molecules, the retention time of rapidly eliminated or metabolized pharmaceutical agents and the membrane penetration of compounds with poor membrane permeability (e.g. blood-brain, cells etc.).

The enzymatic cleavage of the lipid moiety in vivo usually does not occur in the serum but only intracellularly. In addition the carrier moiety with its lecithin-like structure, which is essential for the claimed effect, improves the penetration or membrane permeability of the pharmacologically active substance and exhibits a depot effect. Moreover the gastrointestinal tolerance of the lipid conjugates is considerably better than that of the pure pharmacologically active phosphonocarboxylic acid. The lipid conjugate also exhibits a better penetration through membrane structures during resorption and thus it is more able to overcome the resorption barriers. The same also applies to penetration e.g. of the blood-brain barrier.

In addition the in vivo distribution is improved by a better binding of the conjugate to plasma and tissue proteins. The conjugate is primarily oxidized by normal biotransformation from a thioether to a sulfoxide which, however, due to the equipotent action of the sulfoxide in comparison to the thioether, does not represent a disadvantage. The slow release of the pharmacologically active phosphonocarboxylic acid from the conjugate ensures a low level of active substance that is, however, constant over a long period of time and thus improves the efficacy and/or avoids toxic side-effects. The released pharmacologically active substance in the form of a monophosphate no longer penetrates from the cell due to its high hydrophilicity.

The total body, cell as well as the organ half-lives of the pharmacologically active substance are considerably extended by the conjugation due to the longer retention time of the conjugate in the organism. Due to the lack of cleavage activity in serum and in various organs, almost no or only slight bone marrow and organ toxicity can be observed. It is particularly advantageous that the conjugates of formula I are specifically accumulated in various target organs, tissue or cells.

The compounds of formula I can be used as active substances for the production of pharmaceutical agents which can be used for all diseases in which a high level of pharmacologically active substance in cells, organs or tissues is required or is beneficial. An essential requirement for this system denoted "drug-storage-delivery-targeting" is that the cells which are to respond in accordance with the intended therapy have the cleavage enzyme so that the active substance binds in a first step and is subsequently transported through the cell membrane into the interior of the cell in the process of which the active substance is cleaved to form the physiologically active phosphonocarboxylic acid either essentially simultaneously with transport through the cell membrane or even later partially within the cell. Intracellular cleavage takes place especially in those cases in which the cleavage enzyme is also located within the cell.

Suitable target cells are for example cells of the immunological lymphatic system (e.g. blood leucocytes, monocytes, macrophages, lymphocytes) or infected cells.

Surprisingly it was also found that compounds of the general formula I inhibit the multiplication of DNA or RNA viruses at the level of virus-specific DNA or RNA transcription. The substances can influence the reproduction of retroviruses by inhibiting the enzyme reverse transcriptase (cf. Proc. Natl. Acad. Sci. USA 83, 1911, 1986 and Nature 325, 773, 1987). The inhibitory action on the HI virus, the cause of the immunedeficiency disease AIDS, is of particular therapeutic interest. Nowadays 3'-azidoI3'-deoxythymidine (DE-A-3608606) is approved among others for the treatment of AIDS in ADS patients. However toxic side effects of 3'-azido-3'-deoxythymidine on the bone marrow necessitate blood transfusions in about 50% of the treated patients. The compounds of the general formula I do not have these disadvantages. They have antiviral efficacy without being cytotoxic in pharmacologically relevant doses.

The compounds of the present invention and their pharmaceutical preparations can also be used in combination with other pharmaceutical agents for the treatment and prophylaxis of the above-mentioned infections. Examples of these agents containing further pharmaceutical agents that can be used for the treatment and prophylaxis of HIV infections or diseases which accompany this disease are 3'-azido-3'-deoxythymidine, 2',3'-dideoxynucleosides such as 2',3'-dideoxycytidine, 2',3'-dideoxyadenosine and 2',3'-dideoxyinosine, acyclic nucleosides (e.g. Acyclovir), non-nucleosidic RT inhibitors, protease inhibitors such as e.g. Invirase, interferons such as interferon $\alpha$, $\beta$, $\gamma$, cytokines and interleukins (e.g. interleukin 16), chemokines such as MIP $1\alpha$, MIP $1\beta$, CC1, renal excretion inhibitors such as probenicid, nucleoside transport inhibitors such as dipyridamol as well as immuno-modulators such as interleukin II or stimulating factors such as granulocyte macrophage colony stimulating factors (GM-CSF), granulocyte colony stimulating factors (G-CSF, neutropoetin), thrombopoetin and thrombopoetin-like factors. The compounds of the present invention and the other pharmaceutical agent can be administered individually or simultaneously and optionally in a single or two separate formulations or at different times in order to achieve a synergistic effect.

Alkali, alkaline-earth and ammonium salts of the carboxyl and phosphonate group come above all into consideration as possible salts of the compounds of the general formula I. Lithium, sodium and potassium salts are preferred as the alkali salts. Magnesium and calcium salts come in particular into consideration as alkaline-earth salts. Ammonium salts are understood according to the invention as salts which contain the ammonium ion that can be substituted up to four times by alkyl residues with 1–4 carbon atoms and/or by aralkyl residues preferably by benzyl residues. In this case the substituents can be the same or different.

$R^1$ in formula I preferably denotes a straight-chained, saturated alkylene chain with e equalling 5–12 carbon atoms. Cycl preferably represents a cyclohexyl or cyclopentyl residue or phenyl which is optionally substituted by $C_1$–$C_4$ alkyl or halogen. Indepentent of each other, X and Y are preferably sulfur, sulfinyl, sulfonyl, oxygen or a valency dash. Particularly preferred as X is sulfur and as Y oxygen. The residue —$(CH_2)_e$-Cycl is preferably in the 3-position of the $C_3$ parent substance. e stands for an area between 6 and 10. $(CH_2)_e$-Cycl means most preferably phenylhexyl oder cyclohexl-hexyl. Particularly preferred alkyl residues for $R^2$ are straight-chained or branched, saturated or unsaturated alkyl chains with 8 to 12 carbon atoms. Particularly preferred alkyl residues for $R^2$ are the nonyl, decyl, undecyl or dodecyl group.

Particularly preferred coupled phosphonocarboxylic acids in the claimed conjugates of the general formula I are:

phosphonoformic acid phosphonoacetic acid phosphonopropionic acid

Preferred esters of phosphonoformic acid, phosphonoacetic acid and phosphonopropionic acid are methyl ester, ethyl ester, propyl ester, butyl ester, t-butyl ester and benzyl ester.

The compounds of the general formula I can be prepared by 1. reacting a compound of the general formula II,

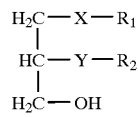

in which $R^1$, $R^2$ and n have the stated meanings, with a compound of the general formula III,

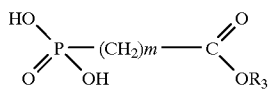

in which m and $R^3$ has the meaning given above and $R^3$ preferrably represents a $C_1$–$C_6$ alkyl residue in the presence of an optionally substituted arylsulfonic acid chloride in an organic base or in the presence of the base in an inert organic solvent and subsequently the carboxylic acid ester is converted into a derivative of formula I or a physiologically compatible salt thereof by means of alkaline saponification; or 2. a mixed anhydride is prepared from a compound of formula III and an alkyl- or arylsulfonic acid chloride and is reacted in the presence of a base in an inert organic solvent or directly in the base with an alcohol of formula II and subsequently the carboxylic acid ester is alkaline saponified, if desired; or 3. a phosphonocarboxylic acid of formula III in which R denotes hydrogen is reacted with an alcohol of formula II in the presence of a base and an optionally substituted arylsulfonic acid chloride and if necessary it is converted into a physiologically compatible ester or salt; or 4. a mixed anhydride of a compound of formula III in which R denotes hydrogen and an alkyl- or arylsulfonic acid chloride is reacted with an alcohol of formula II in the presence of a base optionally in an inert organic solvent and the conjugate is optionally converted into a physiologically compatible salt; or 5. Phosphonic acid dichloride of the general formula IV

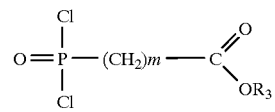

which is synthesized as described in Bhongle et al. (Synthetic Commun. 17, 1071 (1987)) starting from a phosphonic acid bis-trimethylsilyl ester and following reaction with oxalylchloride, reacts afterwards with an alcohol of the general formula II together with a base in molar ratio of 1:1. or 5. a compound of formula III is converted with oxalyl chloride as described in Tetrahedron Letters Vol. 33, No. 49, pp. 7473–7474 into the respective phosphonic acid dichloride of formula IV which is subsequently reacted with an alcohol of formula II in the presence of a base in a molar ratio of 1:1. The phosphonic acid monochloride that forms as an intermediate is saponified to form a semiester and the carboxylic acid ester is converted into a derivative of formula I or a physiologically compatible salt thereof by alkaline saponification.

Compounds of formula II and their production are described in the examples and in EP-0545966.

The pharmaceutical agents containing compounds of formula I for the treatment of for example viral infections can be administered enterally or parenterally in a liquid or solid form. In this case the usual forms of administration come into consideration such as for example tablets, capsules, dragees, syrups, solutions or suspensions. Water is preferably used as an injection medium which contains the additives usually used in injection solutions such as stabilizers, solubilizers and buffers. Such additives are for example tartrate and citrate buffer, ethanol, complexing agents such as ethylene-diamine tetraacetic acid and non-toxic salts thereof, high-molecular polymers such as liquid polyethylene oxide to regulate viscosity. Liquid carriers for injection solutions have to be sterile and are preferably filled into ampoules. Solid carriers are for example starch, lactose, mannitol, methyl cellulose, talcum, highly-dispersed silicic acids, higher molecular fatty acids such as stearic acid, gelatin, agar-agar, calcium phosphate, magnesium stearate, animal and vegetable fats, solid high-molecular polymers such as polyethylene glycols etc. Suitable preparations for oral application can optionally contain flavourings and sweeteners.

The dose can depend on various factors such as manner of application, species, age or individual state. The compounds according to the invention are usually administered in amounts of 0.1–100 mg preferably 0.2–80 mg per day and per kg body weight. It is preferable to divide the daily dose into 2–5 applications, 1–2 tablets with a content of active substance of 0.5–500 mg being administered at each application. The tablets can also be retarded by which means the number of applications can be decreased to 1–3 per day. The content of active substance of the retarded tablets can be 2–1000 mg. The active substance can also be administered as a continuous infusion, amounts of 5–5000 mg per day being normally adequate.

Apart from the compounds mentioned in the examples and compounds derived by combining all meanings of the substituents stated in the claims the following compounds of formula I also come into consideration within the sense of the present invention:

1. [3-(p-Chlorophenyl)hexylmercapto-2-decyloxy)propoxy-hydroxy-phosphinyl-formic acid
2. [3-(p-tert-Butylphenyl)oxy-octylmercapto-2-decyloxy] propoxy-hydroxy-phosphinyl-formic acid
3. [3-(Phenyl)oxy-hexylmercapto-2-decyloxy]propoxy-hydroxy-phosphinyl-formic acid
4. [3-(Phenyl)heptylmercapto-2-decyloxy]propoxy-hydroxy-phosphinyl-formic acid
5. [3-p-Chlorophenyl)oxy-pentylmercapto-2-decyloxy] propoxy-hydroxy-phosphinyl-formic acid
6. [3-(m-Ethylphenyl)decylmercapto-2-decyloxy]propoxy-hydroxy-phosphinyl-formic acid
7. [3-p-tert-Butylphenyl)octylmercapto-2-decyloxy] propoxy-hydroxy-phosphinyl-formic acid
8. [3-(Cyclohexyl)heptylmercapto-2-decyloxy]propoxy-hydroxy-phosphinyl-formic acid
9. [3-Cyclopentyl)nonylmercapto-2-decyloxy]propoxy-hydroxy-phosphinyl-formic acid
10. [3-(Cycloheptyl)octylmercapto-2-decyloxy]propoxy-hydroxy-phosphinyl-formic acid
11. [3-(Cyclohexyl)oxy-pentylmercapto-2-decyloxy] propoxy-hydroxy-phosphinyl-formic acid
12. [3-(Cyclohexyl)mercapto-pentylmercapto-2-decyloxy] propoxy-hydroxy-phosphinyl-formic acid
13. [3-(Phenyl)undecylmercapto-2-decyloxy]propoxy-hydroxy-phosphinyl-formic acid
14. [3-Dodecylmercapto-2-(phenyl)hexylmercapto] propoxy-hydroxy-phosphinyl-formic acid
15. [3-Decyloxy-2-(cyclohexyl)hexylmercapto]propoxy-hydroxy-phosphinyl-formic acid
16. [3-(p-Chlorophenyl)hexylmercapto-2-decyloxy) propoxy-hydroxy-phosphinyl-acetic acid
17. [3-(p-tert-Butylphenyl)oxy-octylmercapto-2-decyloxy] propoxy-hydroxy-phosphinyl-acetic acid
18. [3-(Phenyl)oxy-hexylmercapto-2-decyloxy]propoxy-hydroxy-phosphinyl-acetic acid
19. [3-(Phenyl)heptylmercapto-2-decyloxy]propoxy-hydroxy-phosphinyl-acetic acid
20. [3-p-Chlorophenyl)oxy-pentylmercapto-2-decyloxy] propoxy-hydroxy-phosphinyl-acetic acid
21. [3-(m-Ethylphenyl)decylmercapto-2-decyloxy]propoxy-hydroxy-phosphinyl-acetic acid
22. [3-p-tert-Butylphenyl)octylmercapto-2-decyloxy] propoxy-hydroxy-phosphinyl-acetic acid
23. [3-(Cyclohexyl)heptylmercapto-2-decyloxy]propoxy-hydroxy-phosphinyl-acetic acid
24. [3-Cyclopentyl)nonylmercapto-2-decyloxy]propoxy-hydroxy-phosphinyl-acetic acid
25. [3-(Cycloheptyl)octylmercapto-2-decyloxy]propoxy-hydroxy-phosphinyl-acetic acid
26. [3-(Cyclohexyl)oxy-pentylmercapto-2-decyloxy] propoxy-hydroxy-phosphinyl-acetic acid
27. [3-(Cyclohexyl)mercapto-pentylmercapto-2-decyloxy] propoxy-hydroxy-phosphinyl-acetic acid
28. [3-(Phenyl)undecylmercapto-2-decyloxy]propoxy-hydroxy-phosphinyl-acetic acid
29. [3-Dodecylmercapto-2-(phenyl)hexylmercapto] propoxy-hydroxy-phosphinyl-acetic acid
30. [3-Decyloxy-2-(cyclohexyl)hexylmercapto]propoxy-hydroxy-phosphinyl-acetic acid
31. [3-(p-Chlorophenyl)hexylmercapto-2-decyloxy) propoxy-phosphinyl-propionic acid
32. [3-(p-tert-Butylphenyl)oxy-octylmercapto-2-decyloxy] propoxy-hydroxy-phosphinyl-propionic acid
33. [3-(Phenyl)oxy-hexylmercapto-2-decyloxy]propoxy-hydroxy-phosphinyl-propionic acid
34. [3-(Phenyl)heptylmercapto-2-decyloxy]propoxy-hydroxy-phosphinyl-propionic acid
35. [3-p-Chlorophenyl)oxy-pentylmercapto-2-decyloxy] propoxy-hydroxy-phosphinyl-propionic acid
36. [3-(m-Ethylphenyl)decylmercapto-2-decyloxy]propoxy-hydroxy-phosphinyl-propionic acid
37. [3-p-tert-Butylphenyl)octylmercapto-2-decyloxy] propoxy-hydroxy-phosphinyl-propionic acid
38. [3-(Cyclohexyl)heptylmercapto-2-decyloxy]propoxy-hydroxy-phosphinyl-propionic acid
39. [3-Cyclopentyl)nonylmercapto-2-decyloxy]propoxy-hydroxy-phosphinyl-propionic acid
40. [3-(Cycloheptyl)octylmercapto-2-decyloxy]propoxy-hydroxy-phosphinyl-propionic acid
41. [3-(Cyclohexyl)oxy-pentylmercapto-2-decyloxy] propoxy-hydroxy-phosphinyl-propionic acid
42. [3-(Cyclohexyl)mercapto-pentylmercapto-2-decyloxy] propoxy-hydroxy-phosphinyl-propionic acid
43. [3-(Phenyl)undecylmercapto-2-decyloxy]propoxy-hydroxy-phosphinyl-propionic acid
44. [3-Dodecylmercapto-2-(phenyl)hexylmercapto] propoxy-hydroxy-phosphinyl-propionic acid
45. [3-Decyloxy-2-(cyclohexyl)hexylmercapto]propoxy-hydroxy-phosphinyl-propionic acid
46. ((3-(6-Cyclohexylhexylmercapto)-2-decyloxy)-propoxy)-hydroxyphosphinyl-formic acid butylester
47. ((3-(6-Phenylhexylmercapto)-2-decyloxy)-propoxy)-hydroxyphosphinyl-formic acid ethylester
48. ((3-(6-Phenylhexylmercapto)-2-decyloxy)-propoxy)-hydroxyphosphinyl-formic acid propylester
49. ((3-(6-Phenylhexylmercapto)-2-decyloxy)-propoxy)-hydroxyphosphinyl-formic acid t-butylester
50. ((3-(6-Phenylhexylmercapto)-2-decyloxy)-propoxy)-hydroxyphosphinyl-formic acid (2-dimethylamino) ethylester

EXAMPLE 1

R,S-(3-(6-phenylhexylthio)-2-decyloxy)-propoxy)-hydroxy-phosphinyl-formic acid disodium salt 1 (Ph6S10OP-PFA)

6-Phenyl-1-hexanethiol 13

15.0 g (62.2 mmol) 1-bromo-6-phenyl-hexane (described in the unexamined laid-open patent application of the int. Appl. PCT/EP95/04413) dissolved in 40 ml ethanol was added under a nitrogen atmosphere to a solution of 7.10 g (93.3 mmol) thiourea in 30 ml ethanol. After boiling for 7 hours at reflux temperature, it was allowed to cool to room temperature, admixed with 33 ml concentrated ammonia and heated for 4 h to reflux. Subsequently it was acidified to pH 1 with 15 ml concentrated HCl. It was extracted three times with 200 ml ether each time, washed with water and saturated sodium chloride solution, dried over magnesium sulfate and the solvent was removed in a vacuum. The residue was taken up in dichloromethane, the solid was suction filled, rewashed with dichloromethane and the filtrate was evaporated in a vaccum. 9.80 g (82%) 13 as a colourless oil.

R,S-2-Decyloxy-3-(6-phenylhexylmercapto)-1-propyl-benzoate 14

9.60 g (49.4 mmol) 13 and 6.80 g (49.4 mmol) potassium carbonate were placed in 100 ml methyl ethyl ketone under a nitrogen atmosphere, they were stirred for 15 min and then admixed with 19.7 g (49.4 mmol) 3-bromo-2-decyloxy-1-propyl-benzoate 12 (EP 0545966) and one crystal of potassium iodide. After addition of 5 ml dimethylformamide it was stirred for 48 h at room temperature. The potassium carbonate was aspirated, the precipitate was washed with heptane and the filtrate was concentrated in a vacuum. The residue was taken up in water, extracted with heptane and the organic phase was washed with 0.5 N NaOH, neutralized with water, dried over magnesium sulfate and evaporated. 25.6 (100%) 14 was obtained which was used to synthesize 15 without further purification.

R,S-2-Decyloxy-3-(6-phenylhexylmercapto)-1-propanol 15

A mixture of 25.5 g (49.7 mmol) 14, 30 ml ethanol and 12 ml (60.0 mmol) 5 N NaOH was stirred under nitrogen for a total of 48 hours at room temperature. It was evaporated in a vacuum, taken up in water, extracted with dichloromethane, washed with 1 N NaOH, water, dried over magnesium sulfate and the solvent was removed in a vacuum. 18.9 g (93%) crude product was obtained. It was purified by means of flash chromatography on silica gel (mobile solvent: heptane/ethyl acetate 7:1) in the process of which 12.8 g (63%) 15 was obtained as a colourless oil.

Dichlorophosphinylformic acid methyl ester 16

28.2 g (99.2 mmol) di-(trimethylsilyloxy)-phosphinyl-formic acid methyl ester (Synthetic Commun. 17, 1071 (1987); Tetrahedron Lett. 33, 7473) was dissolved under nitrogen in 150 ml dichloromethane and 5 drops dimethyl-formamide and 37.8 g (0.297 mol) oxalyl chloride was added dropwise at 0° C. within 30 min. After stirring for 2 h at room temperature, the solvent was removed in a vacuum and it was distilled in a high vacuum. 12.1 g (69%) 16, bp 42–45° C./0.19 mbar.

R,S-((3-(6-Phenylhexylthio)-2-decyloxy)-propoxy)-hydroxy-phosphinylformic acid methyl ester 17 (example 12.21).

1.50 g (8.48 mmol) dichlorophosphinylformic acid methyl ester 16 was dissolved in 15 ml dichloromethane under a nitrogen atmosphere and cooled to 5° C. A mixture of 3.50 g (8.48 mmol) R,S-2-decyloxy-3-(6-phenylhexylthio)-1-propanol 15 and 900 mg (8.48 mmol) triethylamine dissolved in 20 ml dichloromethane was added dropwise within 15 min in the process of which the internal temperature increased to 10° C. After 30 min at 10° C. it was stirred for a further 3 h at room temperature and subsequently poured into a solution of 7.85 ml 1 N NaOH and 200 ml ice water. It was extracted twice with 100 ml dichloromethane each time, the combined organic phases were washed with water and dried over magnesium sulfate. After removing the solvent in a vacuum one obtained 4.3 g (95%) of an oil which was purified by flash chromatography on silica gel. After elution of unreacted 15 (1.35 g, mobile solvent: ethyl acetate) development with dichloromethane/methanol 10:1 resulted in a total of 2.52 g (56%) 17 (example 12.21) as a colourless oil.

A mixture of 2.50 g (4.71 mmol) 17, 20 ml ethanol and 20 ml tetrahydrofuran were admixed under nitrogen with 4.7 ml (14.1 mmol) 3 N NaOH. It was stirred for 2 h at room temperature, the solvent was removed on a rotary evaporator, it was taken up in 250 ml water and extracted twice with 50 ml t-butylmethyl ether each time. The aqueous phase was adjusted to pH 8.5 with 1 N HCl and the water was removed by freeze-drying. 2.3 g (87%) 1, melting point 212–214° C.

EXAMPLE 2

R,S-((3-(12-Phenyldodecylthio)-2-decyloxy)-propoxy)-hydroxy-phosphinyl-formic acid disodium salt 2 (Ph12S10OP-PFA)

12-Phenyl-1-dodecanethiol 18

As in the preparation of 13 (example 1) 15.0 g (46.1 mmol) 1-bromo-12-phenyl-dodecane was reacted with 5.3 g (69.2 mmol) thiourea. 11.1 g (87%) 18.

R,S-Decyloxy-3-(12-phenyldodecylthio)-propyl-benzoate 19

10.8 g (38.8 mmol) 18 and 15.3 g (38.8 mmol) 12 yielded 20.0 g (92%) 19.

R,S-Decyloxy-3-(12-phenyldodecylthio)-1-propanol 20

The hydrolysis □f4.40 g (7.37 mmol) 19 with 3.0 ml (15 mmol) 5 N NaOH yielded 3.08 g (85%) 20 as a colourless oil.

3.39 g (52%) R,S-((3-(12-phenyldodecylthio)-2-decyloxy)-propoxy)-hydroxy-phosphinylformic acid methyl ester (example 12.22) was obtained analogously to example 1 as a colourless oil from 1.90 g (9.95 mmol) 16 and 4.90 g (9.95 mmol) R,S-2-decyloxy-3-(12-phenyldodecylthio)-1-propanol 20. Saponification with sodium hydroxide solution (analogously to example 1) yielded 2.90 g (94%) 2 with a melting point of 224° C.

EXAMPLE 3

R,S-((3-(10-Phenyldecylthio)-2-decyloxy)-propoxy)-hydroxy-phosphinyl-formic acid disodium salt 3 (Ph10S10OP-PFA)

0.85 g (23%) R,S-((3-(10-phenyldecylthio)-2-decyloxy)-propoxy)-hydroxy-phospinylformic acid methyl ester (example 12.23) was obtained analogously to example 1 as a colourless resin from 1.10 g (6.29 mmol) 16 and 2.92 g (6.29 mmol) R,S-2-decyloxy-3-(10-phenyldecylthio)-1-propanol. Saponification with sodium hydroxide solution (example 1) yielded 0.71 g (79%) 3 with a melting point of 219–220° C.

EXAMPLE 4

R,S-((3-(5-(4-Chlorophenyl)-pentylthio)-2-decyloxy)-propoxy)-hydroxy-phosphinyl-formic acid disodium salt 4 (ClPh5S10OP-PFA)

3.30 g (97%) R,S-((3-(5-(4-chlorophenyl)-pentylthio)-2-decyloxy)-propoxy)-hydroxy-phosphinyl-formic acid methyl ester (example 12.24) was obtained analogously to example 1 as a colourless oil from 1.10 g (mmol) 16 and 2.70 g (6.20 mmol) R,S-2-decyloxy-3-(5-(4-chlorophenyl)-pentylthio)-1-propanol. Saponification of 2.80 g of the ester with sodium hydroxide solution (example 1) yielded 2.90 g (96%) 4 with a melting point of 170–172° C.

EXAMPLE 5

R,S-((3-(10-(4-t-Butylphenoxy)-decylthio)-2-decyloxy)-propoxy)-hydroxy-phosphinyl-formic acid disodium salt 5 (tBuPhO10S10OP-PFA)

1.92 g (58%) R,S-((3-(5-(4-t-butylphenoxy)-decylthio)-2-decyloxy)-propoxy)-hydroxy-phosphinyl-formic acid methyl ester (example 12.25) was obtained analogously to example 1 as a colourless oil from 1.10 g (6.20 mmol) 16 and 3.34 g (6.20 mmol) R,S-2-decyloxy-3-(5-(4-t-butylphenoxy)-decylthio)-1-propanol. Saponification with sodium hydroxide solution (example 1) yielded 1.90 g (95%) 5.

EXAMPLE 6

R,S-((3-(5-Cyclohexylpentylthio)-2-decyloxy)-propoxy)-hydroxy-phosphinyl-formic acid disodium salt 6 (CH5S10OP-PFA)

2.60 g (81%) R,S-((3-(5-cyclohexylpentylthio)-2-decyloxy)-propoxy)-hydroxy-phosphinyl-formic acid methyl ester (example 12.26) was obtained analogously to example 1 as a colourless oil from 1.10 g (6.20 mmol) 16 and 2.48 g (6.20 mmol) R,S-2-decyloxy-3-(5-cyclohexylpentylthio)-1-propanol. Saponification with sodium hydroxide solution (example 1) yielded 1.50 g (92%) 6 with a melting point of 217–219° C.

EXAMPLE 7

R,S-((3-(6-Cyclohexylhexylthio)-2-decyloxy)-propoxy)-hydroxy-phosphinyl-formic acid disodium salt 7 (CH6S10OP-PFA)

2.80 g (72%) R,S-((3-(6-cyclohexylhexylthio)-2-decyloxy)-propoxy)-hydroxy-phosphinyl-formic acid methyl ester (example 12.27) was obtained analogously to example 1 as a colourless oil from 1.30 g (7.30 mmol) 16 and 3.00 g (7.30 mmol) R,S-2-decyloxy-3-(6-cyclohexylhexylthio)-1-propanol. Saponification of 2.02 g of this ester with sodium hydroxide solution (example 1) yielded 2.00 g (93%) 7 with a melting point of 199–202° C.

EXAMPLE 8

R,S-((3-(12-Cyclohexyldodecylthio)-2-decyloxy)-propoxy)-hydroxy-phosphinyl-formic acid disodium salt 8 (CH12S10OP-PFA)

1.70 g (81%) R,S-((3-(12-cyclohexyldodecylthio)-2-decyloxy)-propoxy)-hydroxy-phosphinyl-formic acid methyl ester (example 12.28) was obtained analogously to example 1 as a colourless oil from 0.55 g (3.10 mmol) 16 and 1.50 g (3.10 mmol) R,S-2-decyloxy-3-(12-cyclohexyldodecylthio)-1-propanol. Saponification of 1.50 g of this ester with sodium hydroxide solution (example 1) yielded 1.10 g (71%) 8 with a melting point of 105–107° C.

EXAMPLE 9

R,S-((3-(8-Cyclohexyloctylthio)-2-decyloxy)-propoxy)-hydroxy-phosphinyl-formic acid disodium salt 9 (CH8S10OP-PFA)

2.40 g (68%) R,S-((3-(8-cyclohexyloctylthio)-2-decyloxy)-propoxy)-hydroxy-phosphinyl-formic acid methyl ester (example 12.29) was obtained analogously to example 1 as a colourless oil from 1.10 g (6.29 mmol) 16 and 2.75 g (6.29 mmol) R,S-2-decyloxy-3-(8-cyclohexyloctylthio)-1-propanol. Saponification of 1.37 g of the ester obtained with sodium hydroxide solution (example 1) yielded 0.95 g (68%) 9, decomp. >250° C.

EXAMPLE 10

R,S-((3-(10-Cyclohexyldecylthio)-2-decyloxy)-propoxy)-hydroxy-phosphinyl-formic acid disodium salt 10 (CH10S10OP-PFA)

1.15 g (37%) R,S-((3-(10-cyclohexyldecylthio)-2-decyloxy)-propoxy)-hydroxy-phosphinyl-formic acid methyl ester (example 12.30) was obtained analogously to example 1 as a colourless oil from 1.10 g (6.29 mmol) 16 and 2.96 g (6.29 mmol) R,S-2-decyloxy-3-(10-cyclohexyldecylthio)-1-propanol. Saponification with sodium hydroxide solution (example 1) yielded 1.06 g (89%) 10 with a melting point of 179–181° C.

EXAMPLE 11

R,S-((3-(5-(4-Chlorophenoxy)-pentylthio)-2-decyloxy)-propoxy)-hydroxy-phosphinyl-formic acid disodium salt 11 (ClPhO5S10OP-PFA)

1.27 g (36%) R,S-((3-(5-(4-chlorophenoxy)-pentylthio)-2-decyloxy)-propoxy)-hydroxy-phosphinyl-formic acid methyl ester (example 12.31) was obtained analogously to example 1 as a colourless oil from 1.10 g (6.29 mmol) 16 and 2.80 g (6.29 mmol) R,S-2-decyloxy-3-(5-(4-chlorophenoxy)-pentylthio)-1-propanol. Saponification with sodium hydroxide solution (example 1) yielded 1 .34 g (%) 11 of a wax-like consistency with a melting point of 175–177° C.

EXAMPLE 12

Analogous to examples 1 to 11, it is possible to synthesize the examples 12.21 to 12.51.

Tab. 1 Selected NMR data and $R_f$-values of the examples 1 to 11 and 12.21 to 12.51

$$\begin{array}{c}
H_2C-S-R_1 \\
| \\
HC-O-C_{10}H_{21} \\
| \\
H_2C-O-P-C \overset{O}{\underset{OR_3}{\diagup}} \\
\phantom{H_2C-O-}O \quad O-M
\end{array}$$

The respective $R_f$-values were measured on Kieselgel 60F254DC-Fertigplatten of Fa. Merck, Darmstadt (Material-Nr. 5715) using a volume of 10 μg/10 μl with the solvent 36 (Isopropanol/Butylacetat/Water/Ammonia 50:30:15:5, v/v). Detection was performed with HCl/Perchloric acid spray reagent. The $^{13}C$-shifts shown refer to carbonyl carbon (Dublett J. at 250 Hz).

| Example | $R_1$ | M | $R^3$ | δ $^{31}P$ (CDCl$_3$) | δ $^{13}C$ (CDCl$_3$) | $R_f$ | Ausbeute |
|---|---|---|---|---|---|---|---|
| 1 | —(CH$_2$)$_6$—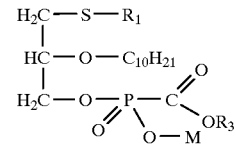 | Na | Na | — | — | 0.33 | 87% |
| 2 | —(CH$_2$)$_{12}$— | Na | Na | 1.8 ppm (D2O) | — | 0.26 | 94% |

-continued

| Example | R₁ | M | R³ | δ ³¹P (CDCl₃) | δ ¹³C (CDCl₃) | R_f | Ausbeute |
|---|---|---|---|---|---|---|---|
| 3 | —(CH₂)₁₀—phenyl | Na | Na | — | — | 0.18 | 78% |
| 4 | —(CH₂)₅—(4-Cl-phenyl) | Na | Na | — | — | 0.30 | 96% |
| 5 | —(CH₂)₁₀—O—(4-t-Bu-phenyl) | Na | Na | — | — | 0.17 | 95% |
| 6 | —(CH₂)₅—cyclohexyl | Na | Na | 8 ppm (DMSO) | — | — | 92% |
| 7 | —(CH₂)₆—cyclohexyl | Na | Na | 1.4 ppm (D2O) | — | 0.26 | 93% |
| 8 | —(CH₂)₁₂—cyclohexyl | Na | Na | 1.8 ppm (D2O) | — | 0.74 | 71% |
| 9 | —(CH₂)₈—cyclohexyl | Na | Na | 2.0 ppm (D2O) | — | 0.72 | 68% |
| 10 | —(CH₂)₁₀—cyclohexyl | Na | Na | — | — | 0.27 | 89% |
| 11 | —(CH₂)₅—O—(4-Cl-phenyl) | Na | Na | — | — | 0.35 | 99% |
| 12.21 | —(CH₂)₆—phenyl | H | CH₃ | −4 ppm | 174 ppm | 0.43 | 45% |
| 12.22 | —(CH₂)₁₂—phenyl | H | Et | −7 ppm | — | — | 52% |
| 12.23 | —(CH₂)₁₀—phenyl | H | CH₃ | −7 ppm | 174 ppm | 0.43 | 39% |
| 12.24 | —(CH₂)₅—(4-Cl-phenyl) | H | CH₃ | −9 ppm | — | — | 40% |
| 12.25 | —(CH₂)₁₀—O—(4-t-Bu-phenyl) | H | CH₃ | −6 ppm | 173 ppm | — | 36% |

-continued

| Example | R₁ | M | R³ | δ ³¹P (CDCl₃) | δ ¹³C (CDCl₃) | R_f | Ausbeute |
|---|---|---|---|---|---|---|---|
| 12.26 | —(CH₂)₅—cyclohexyl | H | CH₃ | −8 ppm | 174 ppm | — | 44% |
| 12.27 | —(CH₂)₆—cyclohexyl | H | CH₃ | −8 ppm | 174 ppm | 0.45 | 44% |
| 12.28 | —(CH₂)₁₂—cyclohexyl | H | CH₃ | −6 ppm | — | — | 42% |
| 12.29 | —(CH₂)₈—cyclohexyl | H | CH₃ | −6 ppm | 173 ppm | — | 40% |
| 12.30 | —(CH₂)₁₀—cyclohexyl | H | CH₃ | −9 ppm | — | — | 37% |
| 12.31 | —(CH₂)₅—O—C₆H₄—Cl | H | CH₃ | −7 ppm | — | — | 36% |
| 12.32 | —(CH₂)₁₀—O—C₆H₅ | H | CH₃ | — | — | 0.71 | 58% |
| 12.33 | —(CH₂)₁₀—O—C₆H₅ | Na | Na | — | — | 0.34 | 98% |
| 12.34 | —(CH₂)₁₀—O—C₆H₄—Cl | H | CH₃ | −5 ppm | 175 ppm | 0.70 | 40% |
| 12.35 | —(CH₂)₁₀—O—C₆H₄—Cl | Na | Na | — | — | 0.35 | 98% |
| 12.36 | —(CH₂)₁₀—O—C₆H₄—CH₃ | H | CH₃ | — | — | 0.70 | 42% |
| 12.37 | —(CH₂)₁₀—O—C₆H₄—CH₃ | Na | Na | — | — | 0.35 | 96% |
| 12.38 | —(CH₂)₁₀—O—C₆H₄—OCH | H | CH₃ | −4 ppm | 175 ppm | 0.70 | 46% |
| 12.39 | —(CH₂)₁₀—O—C₆H₄—OCH | Na | Na | — | — | 0.37 | 98% |

-continued

| Example | R₁ | M | R³ | δ $^{31}$P (CDCl₃) | δ $^{13}$C (CDCl₃) | R_f | Ausbeute |
|---|---|---|---|---|---|---|---|
| 12.40 | —(CH₂)₁₀—O—C₆H₄—CH(CH₃)₂ | H | CH₃ | — | — | — | 11% |
| 12.41 | —(CH₂)₁₀—O—C₆H₄—CH(CH₃)₂ | Na | Na | — | — | 0.34 | 98% |
| 12.42 | —(CH₂)₁₀—O—C₆H₄—C(CH₃)₂CH₂C(CH₃)₃ | H | CH₃ | −4 ppm | 175 ppm | 0.42 | 57% |
| 12.43 | —(CH₂)₁₀—O—C₆H₄—C(CH₃)₂CH₂C(CH₃)₃ | Na | Na | — | — | 0.34 | 93% |
| 12.44 | —(CH₂)₁₂—O—C₆H₄—C(CH₃)₃ | H | CH₃ | −4 ppm | 174 ppm | — | 50% |
| 12.45 | —(CH₂)₁₂—O—C₆H₄—C(CH₃)₃ | Na | Na | — | — | 0.19 | 99% |
| 12.46 | —(CH₂)₉—O—C₆H₄—C(CH₃)₃ | H | CH₃ | −4 ppm | 174 ppm | — | 47% |
| 12.47 | —(CH₂)₉—O—C₆H₄—C(CH₃)₃ | Na | Na | — | — | 0.17 | 99% |
| 12.48 | —(CH₂)₈—O—C₆H₄—C(CH₃)₃ | H | CH₃ | −4 ppm | 175 ppm | 0.71 | 52% |
| 12.49 | —(CH₂)₈—O—C₆H₄—C(CH₃)₃ | Na | Na | — | — | 0.17 | 98% |
| 12.50 | —(CH₂)₁₀—O—(2,4,6-trimethylphenyl) | Na | Na | — | — | 0.35 | 98% |
| 12.51 | —(CH₂)₁₀—O—(2,4,6-trimethylphenyl) | H | CH₃ | −4 ppm | 175 ppm | — | 44% |

EXAMPLE 13

Testing ether lipid-Foscarnet conjugates in the murine cytomegaly virus (MCMV) model in vivo (exp. 951016)

Various ether lipid-Foscarnet conjugates which had variations in the ether lipid moiety of the molecule were tested in vivo in the MCMV model. In this experiment the survival rate after infection with MCMV virus was determined on day +9 after infection in comparison to placebo treated controls (table 2).

The animals were (except in controls I and II) infected intraperitoneally with $2\times10^5$ PFUs/animal on day 0. All animals (except in control I) were immunosuppressed on day -1 using 100 mg/kg cyclophosphamide p.o. All test substances were administered once daily intraperitoneally at a dosage of 30 mg x $kg^{-1}$ x $day^{-1}$ from day 0 (+1 h after infection) to day +8. 10 animals/group were used in each case. The number of surviving animals was determined on day +9.

As can be seen from table 2 only 1 of 10 animals survived to day +9 in control III (group 3) that were placebo treated with PBS. All tested were effective in this animal model. With regard to the survival period there was a significant structure-action relationship for the test substances, TBUPHO10S10OP-PFA, CLPH5S10OP-PFA and PH6S10OP-PFA being the most active compounds.

TABLE 1

Structure-action relationships of ether lipid-Foscarnet conjugates in a MCMV model in vivo[a]

| Group | Substance | MCMV virus (day 0) | Immunosuppression with cyclophosphamide (1 x 100 mg/kg p.o., day -1) | % surviving animals on day +9 |
|---|---|---|---|---|
| 1 | Control 1 | - | - | 100 |
| 2 | Control II | - | + | 100 |
| 3 | Control III | + | + | 10 |
| 4 | TBUPHO10S10OP-PFA | + | + | 80 |
| 5 | CLPH5S10OP-PFA | + | + | 60 |
| 6 | CH5S10OP-PFA | + | + | 30 |
| 7 | CH6S10OP-PFA | + | + | 50 |
| 8 | CH12S10OP-PFA | + | + | 30 |
| 9 | CH8S10OP-PFA | + | + | 30 |
| 10 | PHI2S10OP-PFA | + | + | 40 |
| 11 | PH10S10OP-PFA | + | + | 50 |
| 12 | PH610OP-PFA | + | + | 60 |

[a]Immunosuppression on day -1 with 1 x 100 mg/kg cyclophosphamide p.o. Infection on day 0 with 2 x $10^5$ PFUs/animal i.p. Therapy with 30 mg x $kg^{-1}$ x $day^{-1}$ i.p. from day 0 (+1 h) to day +8 (n = 10 animals per group).

We claim:

1. A compound of the formula

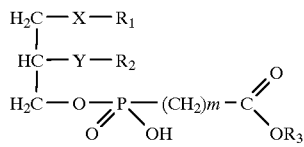

wherein
either
$R_1$ is a group —$(CH_2)_e$-Cycl, wherein $(CH_2)_e$ is straight-chained or branched, and
e is 4–16, wherein one of the carbon atoms in positions 3–16 may be replaced by a heteroatom selected from the group consisting of oxygen, nitrogen and sulfur, and
Cycl is a $C_{5-7}$ cycloalkyl or phenyl, wherein one of the carbon atoms in the Cycl group may be replaced by a nitrogen atom and the Cycl group is unsubstituted or substituted at least once by a substituent independently selected from the group consisting of $C_{1-10}$ alkyl, $C_{1-10}$ alkoxy, $C_{1-10}$ alkylmercapto and halogen, and $R_2$ is hydrogen or a straight-chained or branched saturated or unsaturated $C_{1-20}$ alkyl, or $R_1$ is hydrogen or a straight-chained or branched saturated or unsaturated $C_{1-20}$ alkyl, and $R_2$ is a group —$(CH_2)_e$-Cycl, wherein $(CH_2)_e$ is straight-chained or branched, and
e is 4–16, wherein one of the carbon atoms in positions 3–16 may be replaced by a heteroatom selected from the group consisting of oxygen, nitrogen and sulfur, and
Cycl is a $C_{5-7}$ cycloalkyl or phenyl, wherein one of the carbon atoms in the Cycl group may be replaced by a nitrogen atom and the Cycl group is unsubstituted or substituted at least once by a substituent independently selected from the group consisting of $C_{1-10}$ alkyl, $C_{1-10}$ alkoxy, $C_{1-10}$ alkylmercapto and halogen;

$R_3$ is selected from the group consisting of hydrogen, a straight-chained or branched $C_{1-6}$ alkyl, phenyl, choline, ethanolamine, carnitine, $C_{5-7}$ cycloalkyl, benzyl,

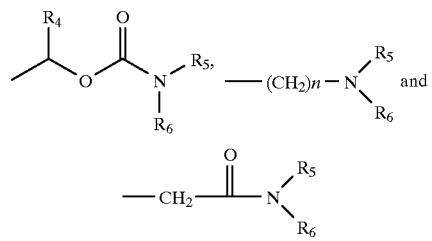

wherein $R_4$ is selected from the group consisting of $C_{1-6}$ alkyl, benzyl and phenyl, $R_5$ and $R_6$ are each independently $C_{1-6}$ alkyl, and n is 1–3;

X and Y are each independently selected from the group consisting of a bond, oxygen, sulfur, oxycarbonyl, carbonyloxy, carbonylamido, amidocarbonyl, sulfinyl and sulfonyl; and m is 0–3, or a tautomer, optical isomer, racemate, physiologically tolerated salt or prodrug thereof.

2. The compound of claim 1, wherein $R_2$ is a straight-chained or branched saturated or unsaturated $C_{8-12}$ alkyl.

3. The compound of claim 1, wherein $R_3$ is other than hydrogen.

4. The compound of claim 1, wherein m is 0–2.

5. The compound of claim 1, wherein $R_3$ is selected from the group consisting of methyl, ethyl, propyl, butyl, t-butyl and benzyl.

6. The compound of claim 1, wherein e is 6–10.

7. The compound of claim 1, wherein X is selected from the group consisting of a bond, oxygen, sulfur, sulfinyl and sulfonyl.

8. The compound of claim 1, wherein Y is selected from the group consisting of a bond, oxygen, sulfur, sulfinyl and sulfonyl.

9. The compound of claim 1, wherein X is sulfur and Y is oxygen.

10. The compound of claim 1, wherein Cycl is selected from the group consisting of cyclohexyl, cyclopentyl and phenyl, wherein the Cycl group is unsubstituted or substituted by $C_{1-4}$ alkyl or halogen.

11. The compound of claim 1, wherein $R_2$ is selected from the group consisting of nonyl, decyl, undecyl and dodecyl.

12. The compound of claim 1, wherein e is 5–12.

13. The compound of claim 1, wherein the group -$(CH_2)_e$-Cycl is hexyl-phenyl or hexyl-$C_{5-7}$ cyclohexyl.

14. A pharmaceutical composition suitable for treating an infection caused by a DNA virus, RNA virus or retrovirus, comprising the compound of claim 12 in combination with a pharmaceutically acceptable carrier.

15. A method of treating an infection caused by a DNA virus, RNA virus or retrovirus in a patient in need of such treatment, comprising administering to the patient an infection treating-effective amount of a compound of claim 1.

16. The method of claim 15, wherein the DNA virus, RNA virus or retrovirus is selected from the group consisting of herpes simplex virus, cytomegaly virus, papova virus, varicella zoster virus, hepatitis virus, Epstein-Barr virus, Toga virus, HTLV-I, HTLV-II, visna virus, HIV-1 and HIV-2.

* * * * *